(12) United States Patent
Lux et al.

(10) Patent No.: US 11,950,918 B1
(45) Date of Patent: Apr. 9, 2024

(54) METHOD AND SYSTEM FOR CALCULATING CONDUCTION VELOCITY OF A CARDIAC ACTIVATION WAVEFRONT

(71) Applicant: Neucures Inc., Los Angeles, CA (US)

(72) Inventors: Robert L. Lux, Park City, UT (US); Rohit Jain, Danville, CA (US)

(73) Assignee: NEUTRACE, INC., Longwood, FL (US)

( * ) Notice: Subject to any disclaimer, the term of this patent is extended or adjusted under 35 U.S.C. 154(b) by 0 days.

(21) Appl. No.: 17/339,997

(22) Filed: Jun. 5, 2021

(51) Int. Cl.
    *A61B 5/367* (2021.01)
    *A61B 5/333* (2021.01)

(52) U.S. Cl.
    CPC .............. *A61B 5/367* (2021.01); *A61B 5/333* (2021.01)

(58) Field of Classification Search
    CPC .......... A61B 5/367; A61B 5/339; A61B 5/343
    See application file for complete search history.

(56) References Cited

U.S. PATENT DOCUMENTS

2016/0106376 A1* 4/2016 Li ..................... A61B 5/6852
    600/373

* cited by examiner

*Primary Examiner* — George R Evanisko
(74) *Attorney, Agent, or Firm* — Vani Moodley, Esq.

(57) ABSTRACT

A method for calculating conduction velocity of a cardiac activation wavefront from electrophysiological ("EP") data points generated by a mapping system during a mapping procedure for a heart is provided. The method comprises for each EP data point comprising a local activation time, and position data defining a location within the heart corresponding to the local activation time: defining a neighborhood of EP points comprising the EP data point and a selection of neighboring EP data points; representing local activation time as a function f(x,y), where x and y our coordinates within a hyperplane defined to contain the neighborhood of EP data points based on the position data for each EP data point in the neighborhood; and calculating conduction velocity at the EP data point as a norm function of a gradient for the function f(x,y).

10 Claims, 8 Drawing Sheets

METHOD AND SYSTEM FOR CALCULATING CONDUCTION VELOCITY OF A CARDIAC ACTIVATION WAVEFRONT

FIELD

Embodiments of the present invention relate to cardiac mapping.

BACKGROUND

Conduction velocity of a cardiac impulse is an important determinant of cardiac tissue health.

BRIEF SUMMARY

In one aspect, a method for calculating conduction velocity of a cardiac activation wavefront, is provided. The method comprises: receiving a plurality of electrophysiological ("EP") data points from a mapping catheter having at least one electrode, each EP data point comprising a recording location and voltage value measured at the recording location for each EP data point, defining a set of neighboring EP data points comprising EP data points selected based on proximity of recording location; defining a surface such that the EP data point and the set of neighboring EP data points all lie on said surface defining LAT as a function f(x,y) on the surface, where x and y are spatial coordinates on the surface; and computing conduction velocity based on the function f(x,y).

In another aspect, a method for calculating conduction velocity of a cardiac activation wavefront from electrophysiological ("EP") data points generated by a mapping system during a mapping procedure for a heart, is provided. The method comprises: for each EP data point comprising a local activation time, and position data defining a location within the heart corresponding to the local activation time: defining a neighborhood of EP points comprising the EP data point and a selection of neighboring EP data points; representing local activation time as a function f(x,y), where x and y our coordinates within a hyperplane defined to contain the neighborhood of EP data points based on the position data for each EP data point in the neighborhood; and calculating conduction velocity at the EP data point as a norm function of a gradient for the function f(x,y) or: $(\sqrt{A^2+B^2})^{-1}$ Other aspects of the invention will be apparent from the detailed description below.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Figure 1:
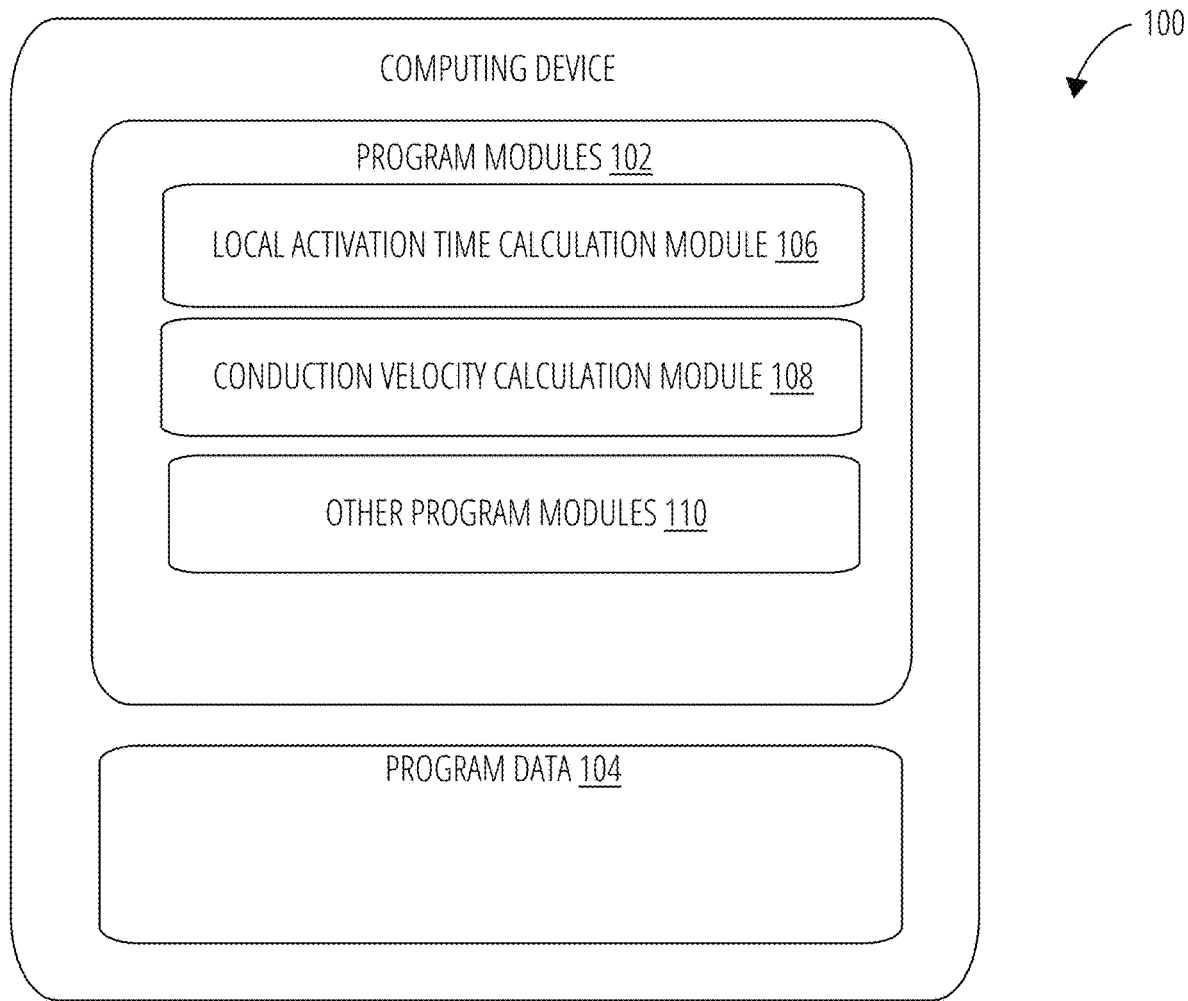
FIG. 1 illustrates an aspect of the subject matter in accordance with one embodiment.

The phrases "in one embodiment", "in various embodiments", "in some embodiments", and the like are used repeatedly. Such phrases do not necessarily refer to the same embodiment. The terms "comprising", "having", and "including" are synonymous, unless the context dictates otherwise.

Reference is now made in detail to the description of the embodiments as illustrated in the drawings. While embodiments are described in connection with the drawings and related descriptions, there is no intent to limit the scope to the embodiments disclosed herein. On the contrary, the intent is to cover all alternatives, modifications and equivalents. In alternate embodiments, additional devices, or combinations of illustrated devices, may be added to or combined, without limiting the scope to the embodiments disclosed herein.

Embodiments of the present invention disclose calculation of conduction velocity of a cardiac activation wavefront.

Although not required, the techniques for calculating conduction velocity of a cardiac activation wavefront is described in the general context of computer-program instructions being executed by a computing device. Program modules generally include routines, programs, objects, components, data structures, etc., that performed the particular tasks or implement particular abstract dated types. While the systems and methods that described in the foregoing context, acts and operations described herein after may also be implemented in hardware.

FIG. 1 shows an exemplary system in the form of a computing device 100 for calculating conduction velocity, in accordance with one embodiment of the invention. Computing device 102 may represent any type of computing device such as a laptop, server, etc. Computing device 100 comprises program modules 102 and program data 104. Program modules 102 may comprise, for example, local activation time calculation module 106 and conduction velocity calculation module 108, and other program modules 110 such as an operating system, etc.

In use, computing device 100 may form part of a cardiac mapping system 700 (which is described later with reference to FIG. 1) and is configured to receive electrocardiogram (ECG) signals and electrophysiological data for a heart. Cardiac mapping system 700 is configured to first select a set of surface electrodes and then drives them with current pulses. While the current pulses are being delivered, electrical activity, such as the voltages measured at least one of the remaining surface electrodes and in vivo electrodes are measured and stored.

In accordance with one embodiment of the invention, cardiac mapping system 700 also includes an electrocardiogram system (not shown) to generate electrocardiograms (ECGs) for a patient. The system 700 also generates electrophysiological (EP) data in the form of EP data points each comprising a recording location within the heart (specified in terms of X, Y, and Z coordinates) and a voltage reading recorded at said location. Thus, each voltage measurement may be associated with position data comprising the spatial location within the heart at which the voltage measurement was made.

In one embodiment, local activation time calculation module 108 calculates a local activation time at each recording location based on analysis of intra-cardiac EGMs to determine the time of min dv/dt as is described in co-pending U.S. patent application Ser. No. 17/073,230 entitled "METHOD AND SYSTEM FOR MEASURING CARDIAC TISSUE HEALTH BASED ON DV/DT MINIMUM OF A DEPOLARIZATION WAVE WITHIN A CARDIAC ELECTROGRAM", which is incorporated herein by reference.

Figure 2:
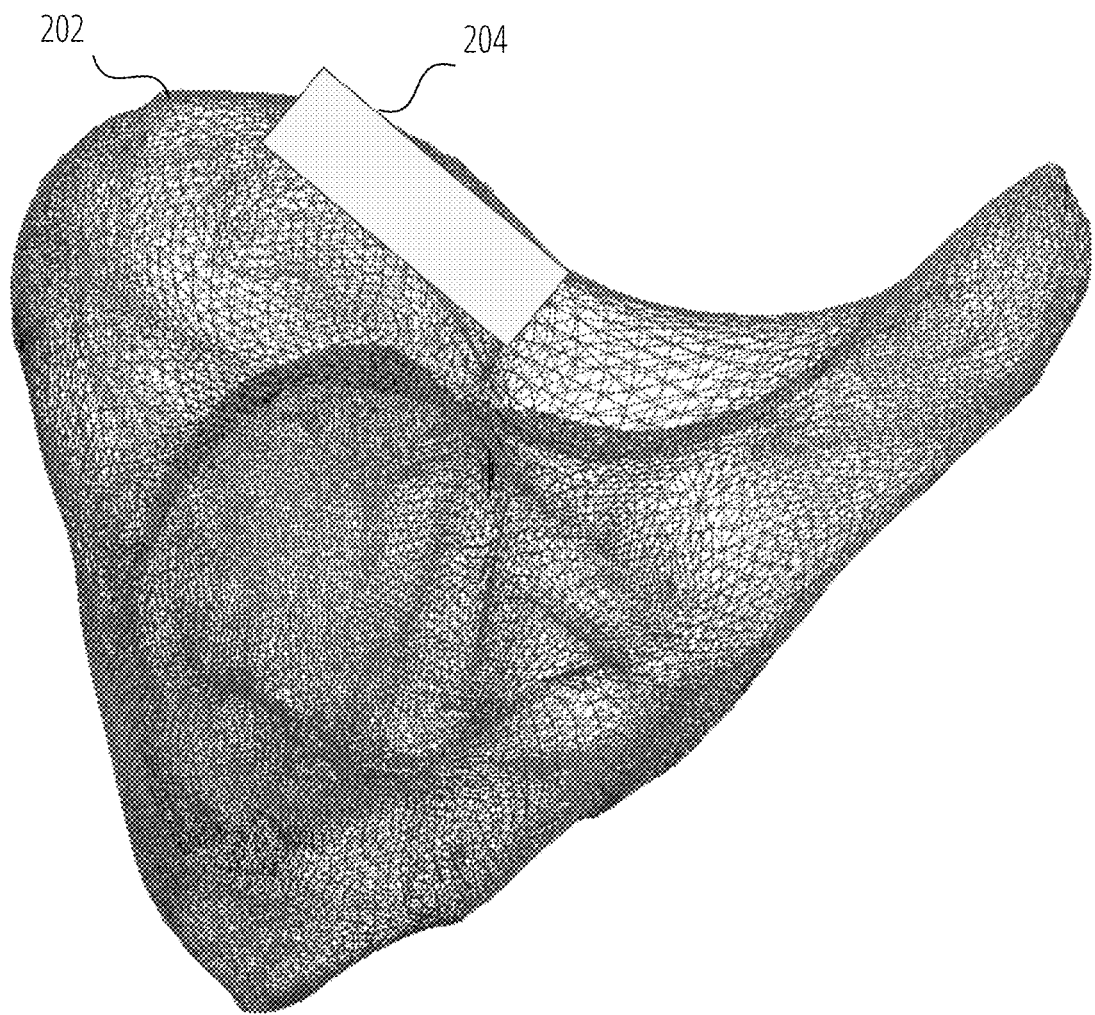
FIG. 2 illustrates an aspect of the subject matter in accordance with one embodiment.

A three-dimensional model of a region of the patient's heart or surrounding vasculature may be created based on the position data. FIG. 2 shows an exemplary three-dimensional model 202. As will be seen, the model 202 defines a three-dimensional surface of the heart and comprises a mesh that approximates the surface of the heart. As will be understood by one of ordinary skill in the art, the mesh may be produced by triangulation techniques and comprises a set of vertices each defining a spatial location on the surface of the heart. The model 202 may be used to show the distribution of local activation times on the surface of the heart.

Figure 3:
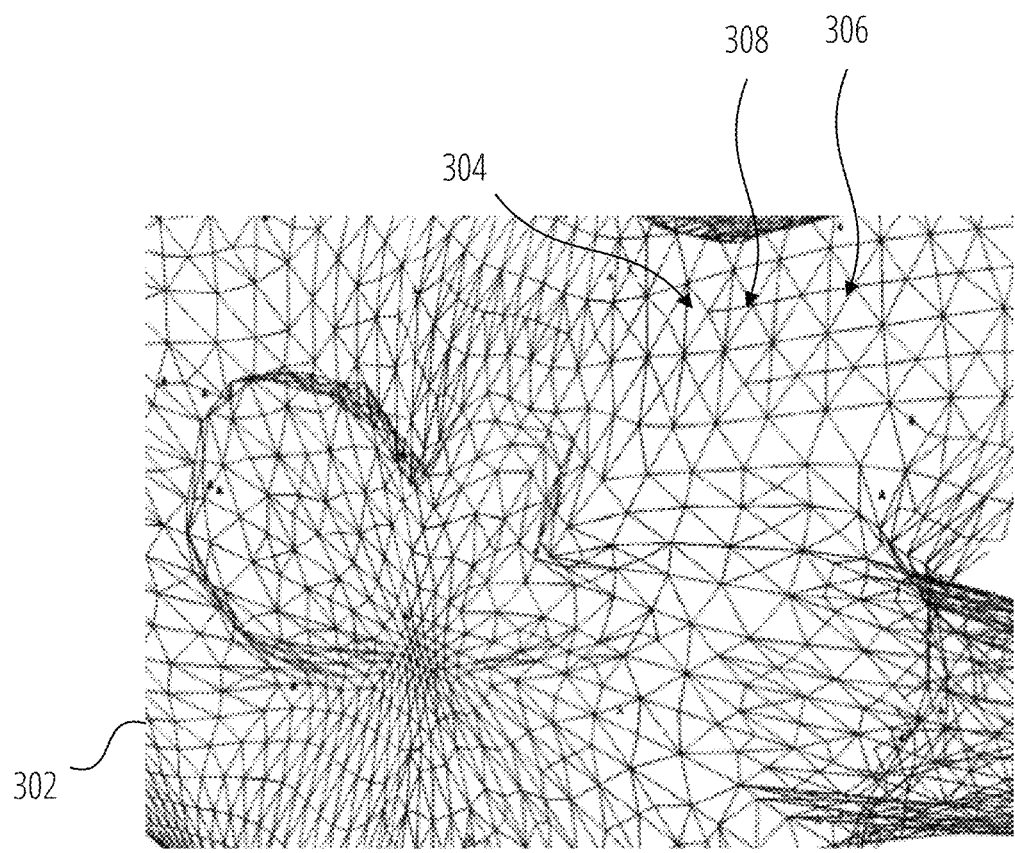
FIG. 3 illustrates an aspect of the subject matter in accordance with one embodiment.

FIG. 3 shows a portion 302 of the model 202 in greater detail so that the vertices may be seen more clearly. For clarity a few of the vertices have been labelled with reference numerals 304, 306, and 308.

Figure 4:
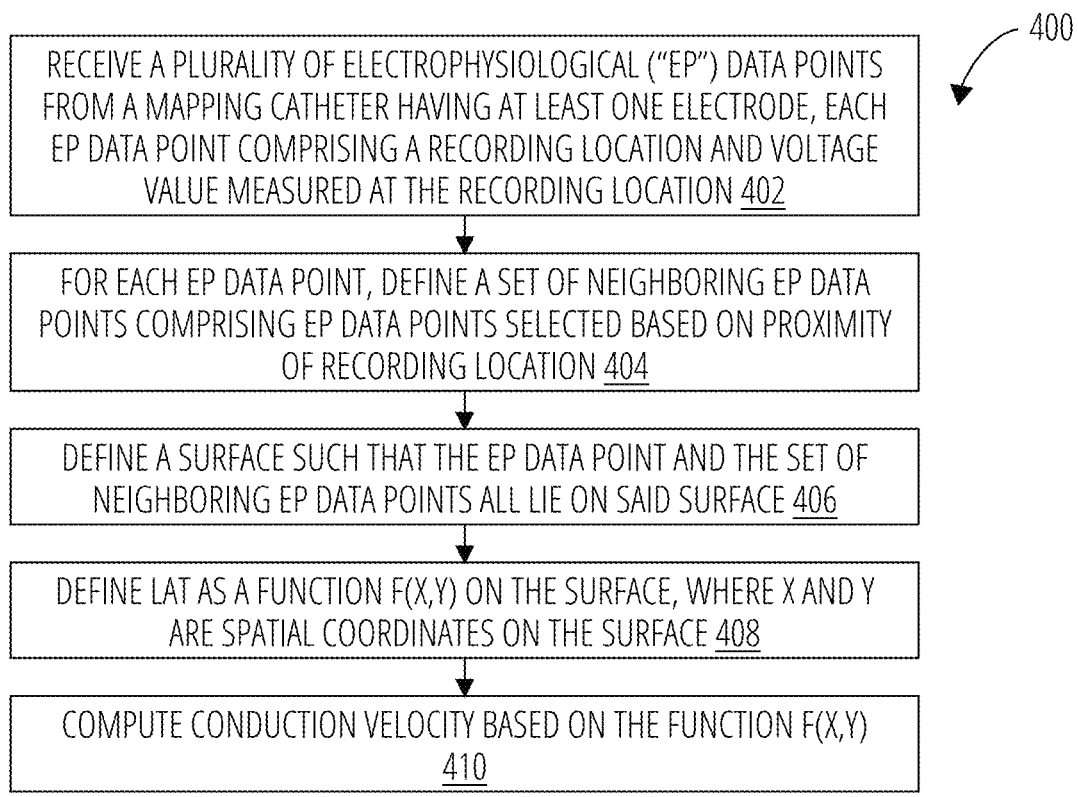
FIG. 4 illustrates a routine 400 for calculating conduction velocity of a cardiac activation wavefront, in accordance with one embodiment.

In one embodiment, conduction velocity calculation module 108 executes a routine 400 illustrated FIG. 4 of the drawings to calculate conduction velocity. In block 402, routine 400 receives a plurality of electrophysiological ("EP") data points from a mapping catheter having at least one electrode, each EP data point comprising a recording location and voltage value measured at the recording location. In block 404, routine 400, for each EP data point, defines a set of neighboring EP data points comprising EP data points selected based on proximity of recording location. In block 406, routine 400 defines a surface such that the EP data point and the set of neighboring EP data points all lie on the surface. In block 408, routine 400 defines LAT as a function f(x,y) on the surface, where x and y are spatial coordinates on the surface. In block 410, routine 400 computes conduction velocity based on the function f(x,y).

Figure 5A:
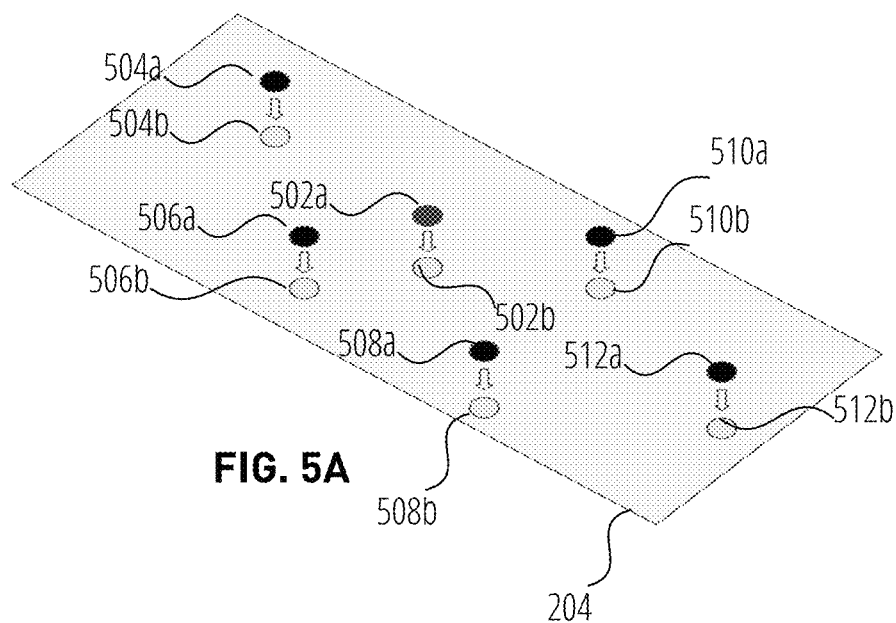
FIG. 5A illustrates an aspect of the subject matter in accordance with one embodiment.

FIG. 5A illustrates how a set of neighboring EP data points may be defined for each EP data point, in accordance with one embodiment of the invention. Referring to FIG. 5A, for each EP point 502a received from cardiac mapping system 700 a few neighboring EP points are added to the neighborhood for said point based on proximity of recording location. In the case of FIG. 5A the points 504a-512a are added to the set of neighboring EP data points for the point 502a. The exact number of points to be added to each set of neighboring EP data points is a matter of implementation detail.

Next, as per block 406, the points of the set of neighboring EP data points are fitted to a surface such each of the points in the set of neighboring EP data points are on the surface or at least close to the surface. Although any surface may be used, in one embodiment, the surface may be a hyperplane defined to contain the set of neighboring EP data points. In some cases, least squares minimization may be performed to find the best hyperplane that fits the set of neighboring EP data points.

In FIG. 5A reference numeral 204 indicates the hyperplane. To lie on the hyperplane the points in the set of neighboring EP data points are fitted to the hyperplane by least squares minimization with the result that point 502a on the mesh becomes point 502b on the hyperplane, point 504a on the mesh becomes point 504b, and so on.

Figure 5B:
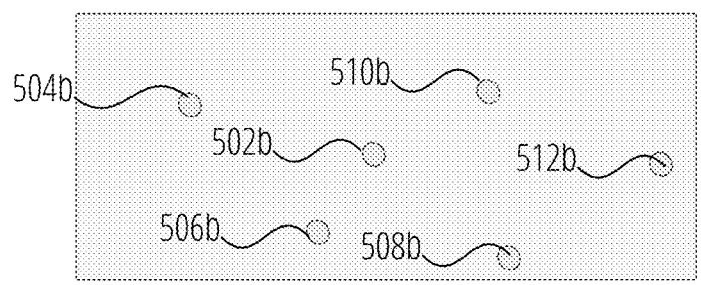
FIG. 5B illustrates an aspect of the subject matter in accordance with one embodiment.

The complete set of neighboring EP data points on the hyperplane is shown in FIG. 5B.

As per block 408, local activation time (LAT) is now a function f(x,y) on the surface (hyperplane) where x,y are coordinates on the surface. In one embodiment, to calculate conduction velocity based on the function f(x,y) said function is first converted into a linear function L(x,y)=Ax+By+C, where X and Y spatial coordinates on the hyperplane, and A, B, and C are constants.

In one embodiment, in block 410 conduction velocity is calculated as the norm of the gradient (A,B) of the linear function L(x,y) or: $(\sqrt{A^2+B^2})^{-1}$.

Figure 6:
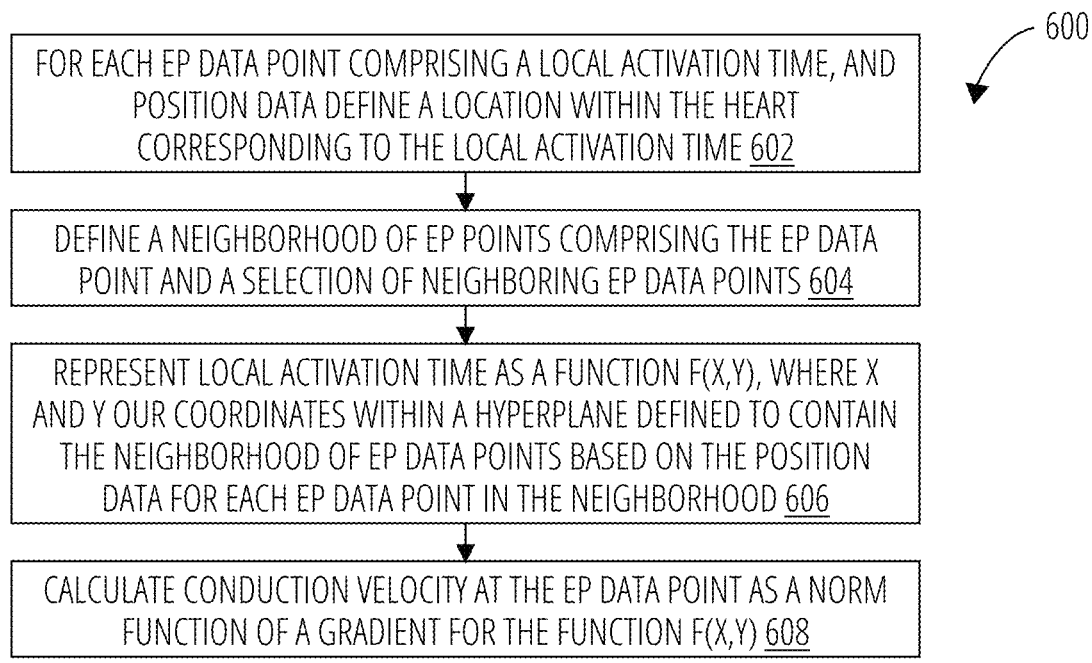
FIG. 6 illustrates a routine 600 for calculating conduction velocity of a cardiac activation wavefront from electrophysiological ("EP") data points generated by a mapping system during a mapping procedure for a heart, in accordance with one embodiment.

FIG. 6 indicates a routine 600 of the conduction velocity calculation module for calculating conduction velocity, in accordance with one embodiment of the invention. In block 602, routine 600 for each EP data point comprising a local activation time, and position data defines a location within the heart corresponding to the local activation time. In block 604, routine 600 defines a neighborhood of EP points comprising the EP data point and a selection of neighboring EP data points. In block 606, routine 600 represents local activation time as a function f(x,y), where x and y our coordinates within a hyperplane defined to contain the neighborhood of EP data points based on the position data for each EP data point in the neighborhood. In block 608, routine 600 calculates conduction velocity at the EP data point as a norm function of a gradient for the function f(x,y).

Routine 600 may be configured to convert into a linear function as described above prior to calculation of conduction velocity.

Figure 7:
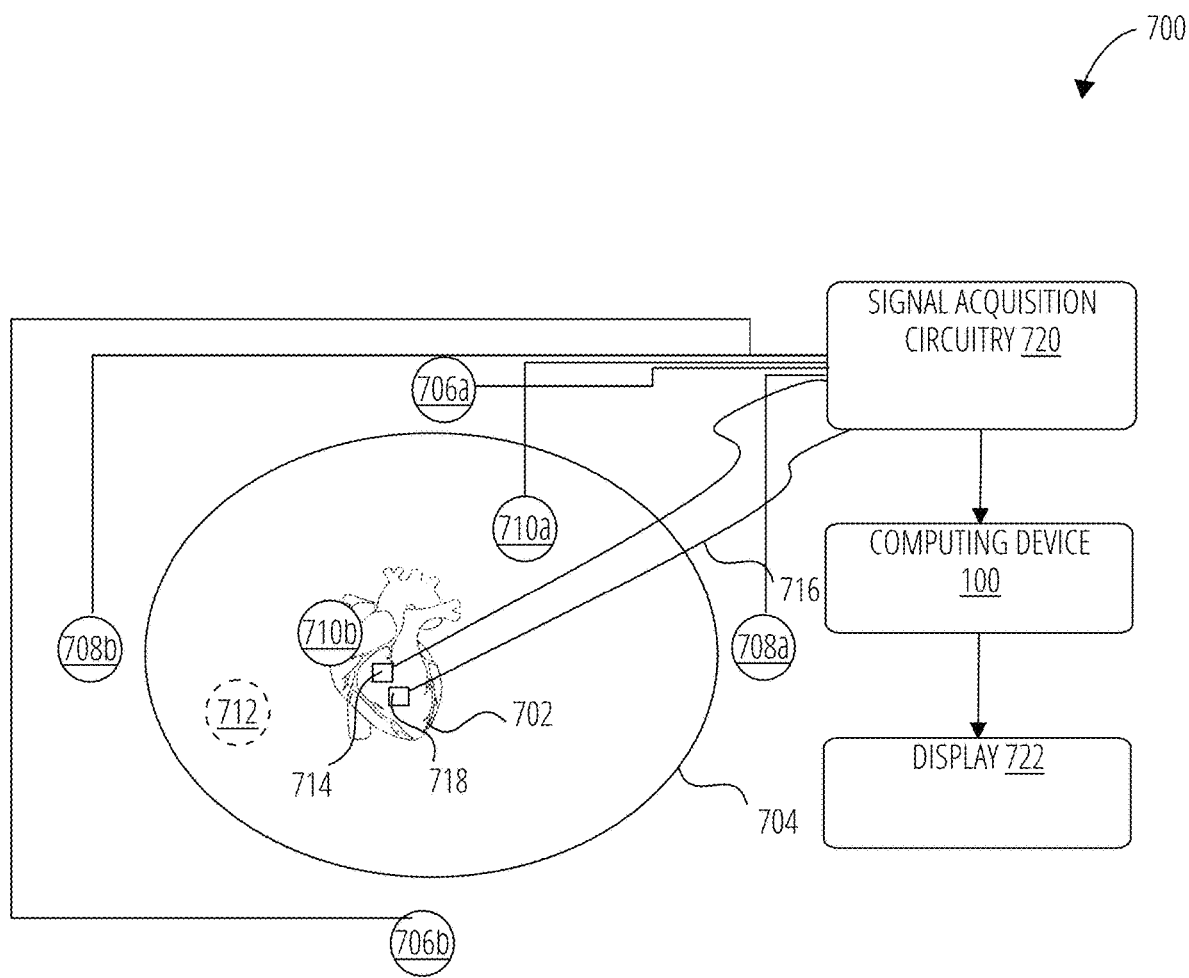
FIG. 7 illustrates an aspect of the subject matter in accordance with one embodiment.

FIG. 7, which shows a schematic diagram of a cardiac mapping system 700 for conducting cardiac electrophysiology studies by navigating a cardiac catheter and measuring electrical activity occurring in a heart 702 of a patient 704 and three-dimensionally mapping the electrical activity and/or information related to or representative of the electrical activity. Cardiac mapping system 700 can be used to help create an anatomical model using one or more electrodes. Cardiac mapping system 700 can also be used to measure electrophysiology data at a plurality of points along a cardiac surface and store the measured data in association with location information for each measurement point at which the electrophysiology data was measured.

The cardiac mapping system 700 comprises a computing device 100, X-axis surface electrodes 706a, 706b, Y-axis surface electrodes 708a, 708b, Z-axis surface electrodes 710a, 710b, surface reference electrode 712, fixed intra-cardiac electrode 714, mapping catheter 716, mapping electrode 718, signal acquisition circuitry 720, and a display 722.

The surface electrodes (e.g., patch electrodes) are shown applied to a surface of patient 704 along an X-axis, a Y-axis, and a Z-axis. Surface reference electrode 712 provides a reference and/or ground electrode for the cardiac mapping system 700. Surface reference electrode 712 may be an alternative to fixed intra-cardiac electrode 714. It should also be appreciated that, in addition, the patient 704 will have most or all of the conventional electrocardiogram (ECG) system leads in place. This ECG information is available to cardiac mapping system 700 although not illustrated in the FIG. 7.

In one embodiment, the localization/mapping system is the EnSite NavX™ navigation and visualization system of St. Jude Medical, Atrial Fibrillation Division, Inc. Other localization systems, however, may be used in connection with the present invention, including for example, the CARTO navigational and location system of Biosense Webster, Inc. and the LOCALISA intracardiac navigation system of Medtronic, Inc. The localization and mapping systems described in the following patents (all of which are hereby incorporated by reference in their entireties) can be used with the present invention: U.S. Pat. Nos. 6,990,370; 6,978,168; 6,947,785; 6,939,309; 6,728,562; 6,640,119; and 5,983,126.

Each surface electrode is coupled to the multiplex switch of signal acquisition circuitry 720 and the pairs of electrodes are selected by software running on computing device 100, which couples the electrodes to a signal generator of the signal acquisition circuitry 720. Computing device 100, for example, may comprise a conventional general-purpose computer, a special-purpose computer, a distributed computer, or any other type of computer. The computing device 100 may comprise one or more processors, such as a single central-processing unit, or a plurality of processing units, commonly referred to as a parallel processing environment.

Generally, three nominally orthogonal electric fields are generated by a series of driven and sensed electric dipoles in order to realize catheter navigation in a biological conductor. Alternately, these orthogonal fields can be decomposed and any pairs of surface electrodes can be driven as dipoles to provide effective electrode triangulation. Additionally, such nonorthogonal methodologies add to the flexibility of the system. For any desired axis, the potentials measured across a fixed intra-cardiac electrode 714 resulting from a predetermined set of drive (source-sink) configurations are combined algebraically to yield the same effective potential as would be obtained by simply driving a uniform current along the orthogonal axes.

Any two of the surface electrodes may be selected as a dipole source and drain with respect to a ground reference, e.g., the surface reference electrode 712 while the unexcited electrodes measure voltage with respect to the ground reference. The mapping/measurement electrode 718 placed in the heart 702 is exposed to the field from a current pulse and is measured with respect to ground, e.g., the surface reference electrode 712. In practice the catheters within the heart may contain multiple electrodes and each electrode potential may be measured. As previously noted, at least one electrode may be fixed to the interior surface of the heart to form a fixed intra-cardiac electrode 714, which is also measured with respect to ground. Data sets from each of the surface electrodes, the internal electrodes, and the virtual electrodes may all be used to determine the location of the measurement electrode 718 or other electrodes within the heart 702.

In summary, the cardiac mapping system 700 first selects a set of surface electrodes and then drives them with current pulses. While the current pulses are being delivered, electrical activity, such as the voltages measured at least one of the remaining surface electrodes and in vivo electrodes are measured and stored. At this point, compensation for artifacts, such as respiration and/or impedance shifting may be performed as indicated above. As described above, various location data points are collected by the cardiac mapping system 700 that are associated with multiple electrode locations (e.g., endocardial electrode locations). Each point in the set has coordinates in space.

Figure 8:
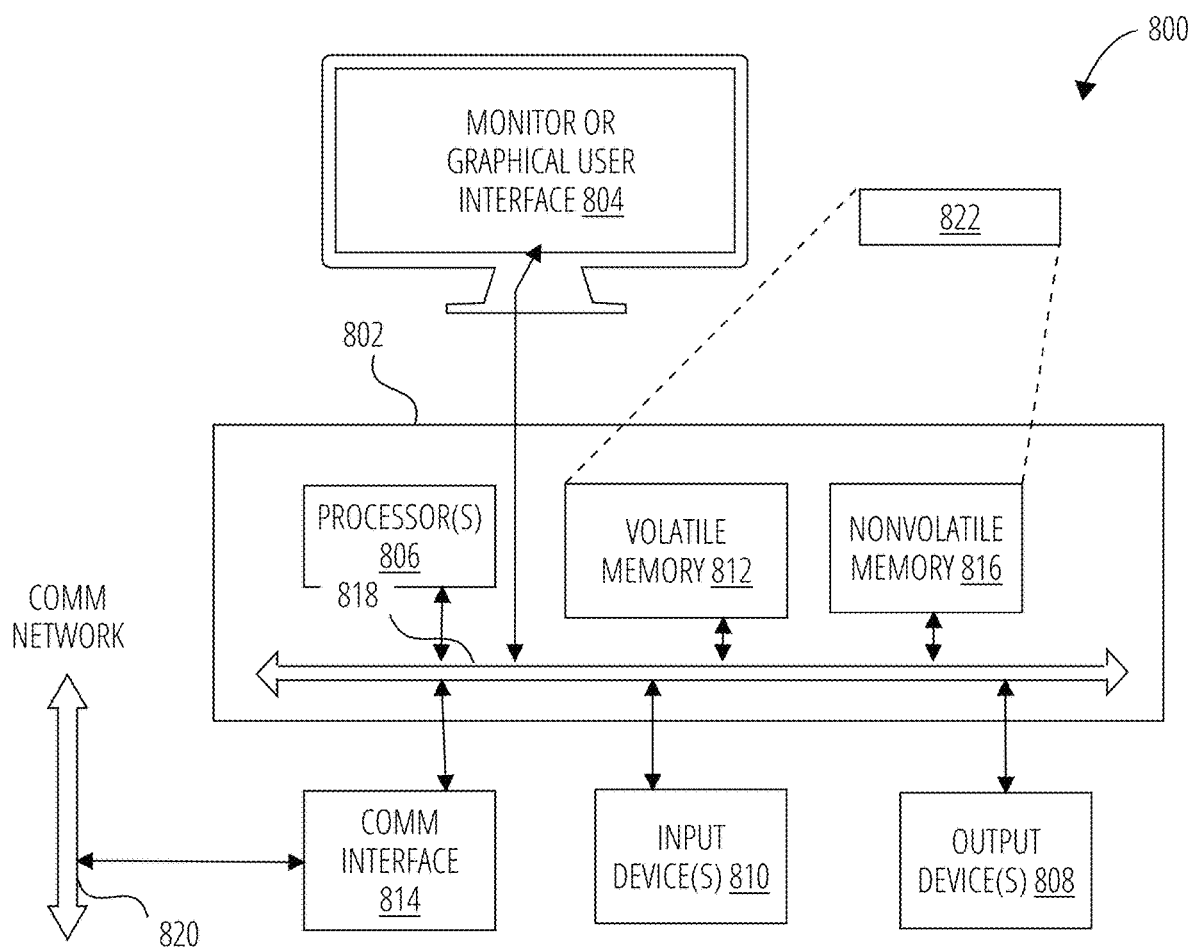
FIG. 8 is an example block diagram of a computing device 100 that may incorporate embodiments of the present invention.

FIG. 8 is an example block diagram of hardware for the computing device 100 in accordance with one embodiment of the present invention. FIG. 8 is merely illustrative of a machine system to carry out aspects of the technical processes described herein and does not limit the scope of the claims. One of ordinary skill in the art would recognize other variations, modifications, and alternatives. In one embodiment, the computing device 100 typically includes a monitor or graphical user interface 804, a data processing system 802, a communication network interface 814, input device(s) 810, output device(s) 808, and the like.

As depicted in FIG. 8, the data processing system 802 may include one or more processor(s) 806 that communicate with a number of peripheral devices via a bus subsystem 818. These peripheral devices may include input device(s) 810, output device(s) 808, communication network interface 814, and a storage subsystem, such as a volatile memory 812 and a nonvolatile memory 816.

The volatile memory 812 and/or the nonvolatile memory 816 may store computer-executable instructions and thus forming logic 822 that when applied to and executed by the processor(s) 806 implement embodiments of the processes disclosed herein.

The input device(s) 810 include devices and mechanisms for inputting information to the data processing system 802. These may include a keyboard, a keypad, a touch screen incorporated into the monitor or graphical user interface 804, audio input devices such as voice recognition systems, microphones, and other types of input devices. In various embodiments, the input device(s) 810 may be embodied as a computer mouse, a trackball, a track pad, a joystick, wireless remote, drawing tablet, voice command system, eye tracking system, and the like. The input device(s) 810 typically allow a user to select objects, icons, control areas, text and the like that appear on the monitor or graphical user interface 804 via a command such as a click of a button or the like.

The output device(s) 808 include devices and mechanisms for outputting information from the data processing system 802. These may include the monitor or graphical user interface 804, speakers, printers, infrared LEDs, and so on as well understood in the art.

The communication network interface 814 provides an interface to communication networks (e.g., communication network 820) and devices external to the data processing system 802. The communication network interface 814 may serve as an interface for receiving data from and transmitting data to other systems. Embodiments of the communication network interface 814 may include an Ethernet interface, a modem (telephone, satellite, cable, ISDN), (asynchronous) digital subscriber line (DSL), FireWire, USB, a wireless communication interface such as BlueTooth or WiFi, a near field communication wireless interface, a cellular interface, and the like.

The communication network interface 814 may be coupled to the communication network 820 via an antenna, a cable, or the like. In some embodiments, the communication network interface 814 may be physically integrated on a circuit board of the data processing system 802, or in some cases may be implemented in software or firmware, such as "soft modems", or the like.

The computing device 200 may include logic that enables communications over a network using protocols such as HTTP, TCP/IP, RTP/RTSP, IPX, UDP and the like.

The volatile memory 812 and the nonvolatile memory 816 are examples of tangible media configured to store computer readable data and instructions to implement various embodiments of the processes described herein. Other types of tangible media include removable memory (e.g., pluggable USB memory devices, mobile device SIM cards), optical storage media such as CD-ROMS, DVDs, semiconductor memories such as flash memories, non-transitory read-only-memories (ROMS), battery-backed volatile memories, networked storage devices, and the like. The volatile memory 812 and the nonvolatile memory 816 may be configured to store the basic programming and data constructs that provide the functionality of the disclosed processes and other embodiments thereof that fall within the scope of the present invention.

Logic 822 that implements embodiments of the present invention may be stored in the volatile memory 812 and/or the nonvolatile memory 816. Said logic 822 may be read from the volatile memory 812 and/or nonvolatile memory 816 and executed by the processor(s) 806. The volatile memory 812 and the nonvolatile memory 816 may also provide a repository for storing data used by the logic 822.

The volatile memory 812 and the nonvolatile memory 816 may include a number of memories including a main random-access memory (RAM) for storage of instructions and data during program execution and a read only memory (ROM) in which read-only non-transitory instructions are stored. The volatile memory 812 and the nonvolatile memory 816 may include a file storage subsystem providing persistent (non-volatile) storage for program and data files. The volatile memory 812 and the nonvolatile memory 816 may include removable storage systems, such as removable flash memory.

The bus subsystem 818 provides a mechanism for enabling the various components and subsystems of data processing system 802 communicate with each other as intended. Although the communication network interface 814 is depicted schematically as a single bus, some embodiments of the bus subsystem 818 may utilize multiple distinct busses.

It will be readily apparent to one of ordinary skill in the art that the computing device 200 may be a device such as a smartphone, a desktop computer, a laptop computer, a rack-mounted computer system, a computer server, or a tablet computer device. As commonly known in the art, the computing device 200 may be implemented as a collection of multiple networked computing devices. Further, the computing device 200 will typically include operating system logic (not illustrated) the types and nature of which are well known in the art.

Terms used herein should be accorded their ordinary meaning in the relevant arts, or the meaning indicated by their use in context, but if an express definition is provided, that meaning controls.

"Circuitry" in this context refers to electrical circuitry having at least one discrete electrical circuit, electrical circuitry having at least one integrated circuit, electrical circuitry having at least one application specific integrated circuit, circuitry forming a general purpose computing device configured by a computer program (e.g., a general purpose computer configured by a computer program which at least partially carries out processes or devices described herein, or a microprocessor configured by a computer program which at least partially carries out processes or devices described herein), circuitry forming a memory device (e.g., forms of random access memory), or circuitry forming a communications device (e.g., a modem, communications switch, or optical-electrical equipment).

"Firmware" in this context refers to software logic embodied as processor-executable instructions stored in read-only memories or media.

"Hardware" in this context refers to logic embodied as analog or digital circuitry.

"Logic" in this context refers to machine memory circuits, non-transitory machine-readable media, and/or circuitry which by way of its material and/or material-energy configuration comprises control and/or procedural signals, and/or settings and values (such as resistance, impedance, capacitance, inductance, current/voltage ratings, etc.), that may be applied to influence the operation of a device. Magnetic media, electronic circuits, electrical and optical memory (both volatile and nonvolatile), and firmware are examples of logic. Logic specifically excludes pure signals or software per se (however does not exclude machine memories comprising software and thereby forming configurations of matter).

"Software" in this context refers to logic implemented as processor-executable instructions in a machine memory (e.g. read/write volatile or nonvolatile memory or media).

Herein, references to "one embodiment" or "an embodiment" do not necessarily refer to the same embodiment, although they may. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively, unless expressly limited to a single one or multiple ones. Additionally, the words "herein," "above," "below" and words of similar import, when used in this application, refer to this application as a whole and not to any particular portions of this application. When the claims use the word "or" in reference to a list of two or more items, that word covers all of the following interpretations of the word: any of the items in the list, all of the items in the list and any combination of the items in the list, unless expressly limited to one or the other. Any terms not expressly defined herein have their conventional meaning as commonly understood by those having skill in the relevant art(s).

Various logic functional operations described herein may be implemented in logic that is referred to using a noun or noun phrase reflecting said operation or function. For example, an association operation may be carried out by an "associator" or "correlator". Likewise, switching may be carried out by a "switch", selection by a "selector", and so on.

The invention claimed is:

1. A method for calculating conduction velocity of a cardiac activation wavefront, comprising:
   driving, with current pulses, a mapping catheter having at least one electrode;
   sensing a plurality of electrophysiological ("EP") data points using the mapping catheter driven due to the current pulses, each EP data point of the plurality of EP data points comprising a recording location and a voltage value measured at the recording location;
   generating a three-dimensional model of a heart of a patient using the received plurality of EP data points;
   selecting, for each EP data point of the plurality of EP data points, a set of neighboring EP data points from the plurality of EP data points based on proximity of the recording location;

defining a surface on the generated three-dimensional model of the heart such that each EP data point of the plurality of EP data points and the corresponding set of neighboring EP data points all lie on said surface;

defining a local activation time (LAT) for each EP data point of the plurality of EP data points as a function f(x,y) on the surface, where x and y are spatial coordinates on the surface; and computing conduction velocity at each EP data point of the plurality of EP data points as a norm function of a gradient for the function f(x,y).

2. The method of claim 1, wherein the surface is a hyperplane.

3. The method of claim 1, wherein computing the conduction velocity comprises converting the function f(x,y) into a linear function L(x,y)=Ax+By+C, wherein x and y are spatial coordinates on the hyperplane, and A, B, and C are constants.

4. The method of claim 3, wherein computing the conduction velocity comprises calculating the gradient L(x,y)=(A,B) for the function f(x,y).

5. The method of claim 4, wherein computing the conduction velocity comprises solving for the norm of (A,B).

6. A computing apparatus comprising:
a processor;
a mapping catheter having at least one electrode; and
a memory storing instructions that, when executed by the processor, configure the apparatus to:
drive the mapping catheter with current pulses;
sense a plurality of electrophysiological ("EP") data points using the mapping catheter driven due to the current pulses, each EP data point of the plurality of EP data points comprising a recording location and a voltage value measured at the recording location;
generating a three-dimensional model of a heart of a patient using the received plurality of EP data points;
select, for each EP data point of the plurality of EP data points, a set of neighboring EP data points from the plurality of EP data points based on proximity of the recording location;
define a surface on the generated three-dimensional model of the heart such that each EP data point of the plurality of EP data points and the corresponding set of neighboring EP data points all lie on said surface;
define a local activation time (LAT) for each EP data point of the plurality of EP data points as a function f(x,y) on the surface, where x and y are spatial coordinates on the surface; and
compute conduction velocity at each EP data point of the plurality of EP data points as a norm function of a gradient for the function f(x,y).

7. The computing apparatus of claim 6, wherein the surface is a hyperplane.

8. The computing apparatus of claim 6, wherein computing the conduction velocity comprises conversion of the function f(x,y) into a linear function L(x,y)=Ax+By+C, wherein x and y are spatial coordinates on the hyperplane, and A, B, and C are constants.

9. The computing apparatus of claim 8, wherein computing the conduction velocity comprises calculation of the gradient L(x,y)=(A,B) for the function f(x,y).

10. The computing apparatus of claim 9, wherein computing the conduction velocity comprises solve for the norm of (A,B).

* * * * *